United States Patent
Ohshima et al.

(10) Patent No.: US 7,858,615 B2
(45) Date of Patent: Dec. 28, 2010

(54) (S)-(-)-1-(4-FLUOROISOQUINOLIN-5-YL)SULFONYL-2-METHYL-1,4-HOMO-PIPERAZINE HYDROCHLORIDE DIHYDRATE

(75) Inventors: Takeshi Ohshima, Kounosu (JP); Hiroyoshi Hidaka, Nagoya (JP); Masami Shiratsuchi, Musashimurayama (JP); Kazuhiro Onogi, Iruma (JP); Toshiaki Oda, Higashimurayama (JP)

(73) Assignees: Kowa Co., Ltd., Nagoya-shi (JP); D. Western Therapeutics Institute, Inc., Nagoya-shi (JP)

( * ) Notice: Subject to any disclaimer, the term of this patent is extended or adjusted under 35 U.S.C. 154(b) by 825 days.

(21) Appl. No.: 11/720,288

(22) PCT Filed: Nov. 29, 2005

(86) PCT No.: PCT/JP2005/021844

§ 371 (c)(1),
(2), (4) Date: May 25, 2007

(87) PCT Pub. No.: WO2006/057397

PCT Pub. Date: Jun. 1, 2006

(65) Prior Publication Data

US 2008/0021018 A1    Jan. 24, 2008

(30) Foreign Application Priority Data

Nov. 29, 2004 (JP) ............................. 2004-344271

(51) Int. Cl.
*A61P 9/10* (2006.01)
*A61K 31/551* (2006.01)
*C07D 401/12* (2006.01)

(52) U.S. Cl. ...................................... 514/218; 540/575
(58) Field of Classification Search ................ 514/218; 540/575

See application file for complete search history.

(56) References Cited

U.S. PATENT DOCUMENTS 6,153,608 A * 11/2000 Hidaka et al. ............... 514/218

FOREIGN PATENT DOCUMENTS

| JP | 9 12573 | 1/1997 |
| WO | 97 02260 | 1/1997 |
| WO | 99 20620 | 4/1999 |
| WO | WO 99/20620 | 4/1999 |

* cited by examiner

*Primary Examiner*—Brenda L Coleman
(74) *Attorney, Agent, or Firm*—Oblon, Spivak, McClelland, Maier & Neustadt, L.L.P.

(57) ABSTRACT

The present invention is directed to (S)-(−)-1-(4-fluoroisoquinolin-5-yl)sulfonyl-2-methyl-1,4-homopiperazine hydrochloride dihydrate, to a method producing the dihydrate, and to a drug composition containing the dihydrate. The compound of the present invention has less hygroscopicity as compared with (S)-(−)-1-(4-fluoroisoquinolin-5-yl)sulfonyl-2-methyl-1,4-homopiperazine hydrochloride anhydrous crystals and thus, exhibits excellent chemical stability.

10 Claims, 8 Drawing Sheets

(S)-(-)-1-(4-FLUOROISOQUINOLIN-5-YL)SULFONYL-2-METHYL-1,4-HOMOPIPERAZINE HYDROCHLORIDE DIHYDRATE

This application is a national stage entry under 35 U.S.C. §371 of PCT/JP05/21844, filed Nov. 29, 2005.

TECHNICAL FIELD

The present invention relates to (S)-(-)-1-(4-fluoroisoquinolin-5-yl)sulfonyl-2-methyl-1,4-homopiperazine hydrochloride dihydrate, which has excellent hygroscopic stability

BACKGROUND ART (S)-(-)-1-(4-fluoroisoquinolin-5-yl)sulfonyl-2-methyl-1,4-homopiperazine hydrochloride is a compound represented by formula (1):

(1)

(see Patent Document 1) and assumes the form of anhydrous crystals which are water-soluble. The compound (1) is known to be a useful drug for preventing and treating cerebrovascular disorders such as cerebral infarction, cerebral hemorrhage, subarachnoidal hemorrhage, and cerebral edema, particularly for suppressing cerebrovasospasm-related diseases such as cerebral stroke (see Patent Document 1).

Conventionally, only (S)-(-)-1-(4-fluoroisoquinolin-5-yl)sulfonyl-2-methyl-1,4-homopiperazine hydrochloride anhydrous crystals (hereinafter may be referred to simply as "anhydrous crystals") are known to be the crystal form of compound (1) (see Patent Document 1). The anhydrous crystals have a water content, as determined through Karl Fischer's method, of 1 wt. % (hereinafter referred to simply as "%") or less.

Figure 5:
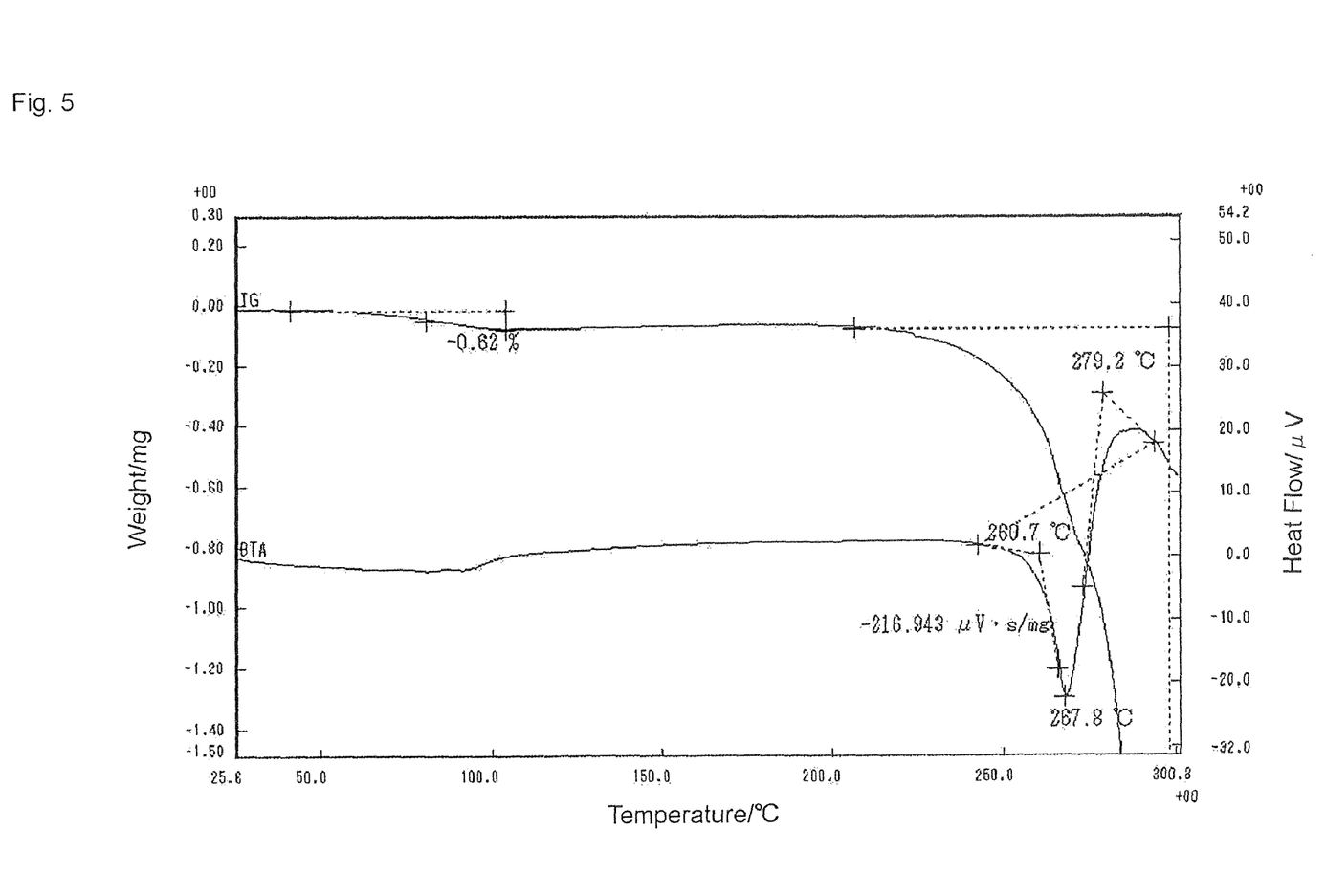
FIG. 5 is a graph showing thermal analyses of (S)-(−)-1-(4-fluoroisoquinolin-5-yl)sulfonyl-2-methyl-1,4-homopiperazine hydrochloride (anhydrous crystals).

However, water content of the anhydrous crystals increases with elapsed time at 25° C. and a relative humidity (RH) of 92%, and eventually reaches about 40% (FIG. 5). When the anhydrous crystals are stored under humid conditions (relative humidity higher than 50%), the anhydrous crystal structure thereof changes due to a hygroscopic phenomenon, concomitant with change in volume of the crystals. In other words, the anhydrous crystals undergo change in crystal structure via a hygroscopic phenomenon.

As has been generally known, when a main drug component or an excipient has problematic hygroscopicity or other problems, change in weight and in crystal form of the compound occurs, resulting in change in volume, possibly causing changes in hardness and cracks in tablets. Such a phenomenon is disadvantageous in the production of tablets. Thus, from the viewpoint of drug preparation and storage of drugs, compounds free from problems in hygroscopicity and other properties are used. In addition, change in crystal form caused by water absorption may impair stability and bioavailability of the compound. As a compound which is required to have very high purity to be suitably used as a base material for a medicine, the above problems need to be solved.

Since the anhydrous crystals of compound (1) have a drawback of problematic hygroscopicity, the anhydrate must be stored under rigorous moisture control. However, such rigorous control is difficult to carry out in an actual situation. Thus, there is a demand for a compound to be used as base material for a medicine as described above which has low hygroscopicity and high storage stability.

Patent Document 1: International Publication WO 99/20620 pamphlet

DISCLOSURE OF THE INVENTION

Problems to be Solved by the Invention

Thus, an object of the present invention is to improve chemical instability of (S)-(-)-1-(4-fluoroisoquinolin-5-yl)sulfonyl-2-methyl-1,4-homopiperazine hydrochloride anhydrous crystals, the chemical instability including change in weight and in crystal form of a compound as a base material for a medicine caused by hygroscopicity of the anhydrous crystals as well as change in volume of the crystals concomitant therewith.

Means for Solving the Problems

Under such circumstances, the present inventors have carried out extensive studies, and have found that (S)-(-)-1-(4-fluoroisoquinolin-5-yl)sulfonyl-2-methyl-1,4-homopiperazine hydrochloride dihydrate (hereinafter may be referred to simply as "dihydrate" or "dihydrate crystals"), which is a novel compound represented by formula (2):

(2)

exhibits excellent hygroscopic stability; assumes the form of virtually non-hygroscopic crystals, whereby change in weight and in crystal form induced by absorption of moisture as well as change in volume concomitant therewith are prevented; and exhibits high thermal stability. The present invention has been accomplished on the basis of this finding.

Accordingly, the present invention provides (S)-(-)-1-(4-fluoroisoquinolin-5-yl)sulfonyl-2-methyl-1,4-homopiperazine hydrochloride dihydrate, which is a novel compound.

The present invention also provides a method for producing (S)-(-)-1-(4-fluoroisoquinolin-5-yl)sulfonyl-2-methyl-1,4-homopiperazine hydrochloride dihydrate, comprising dissolving (S)-(-)-1-(4-fluoroisoquinolin-5-yl)sulfonyl-2-methyl-1,4-homopiperazine hydrochloride in water at 50 to 100° C., subsequently, adding a hydrophilic organic solvent to the solution, and cooling the mixture to 0 to 30° C.

The present invention also provides a drug composition comprising (S)-(-)-1-(4-fluoroisoquinolin-5-yl)sulfonyl-2-methyl-1,4-homopiperazine hydrochloride dihydrate and a pharmaceutically acceptable carrier.

The present invention also provides a medicine comprising (S)-(−)-1-(4-fluoroisoquinolin-5-yl)sulfonyl-2-methyl-1,4-homopiperazine hydrochloride dihydrate.

The present invention also provides use of (S)-(−)-1-(4-fluoroisoquinolin-5-yl)sulfonyl-2-methyl-1,4-homopiperazine hydrochloride dihydrate for manufacture of a medicine.

The present invention also provides a method for preventing or treating cerebrovascular disorders comprising administering to a subject in need thereof an effective amount of (S)-(−)-1-(4-fluoroisoquinolin-5-yl)sulfonyl-2-methyl-1,4-homopiperazine hydrochloride dihydrate.

Effects of the Invention (S)-(−)-1-(4-fluoroisoquinolin-5-yl)sulfonyl-2-methyl-1,4-homopiperazine hydrochloride dihydrate, which is a novel compound of the present invention, is non-hygroscopic. Therefore, problems originating from moisture absorption can be avoided. In addition, the dihydrate has excellent thermal stability. Thus, the dihydrate of the present invention is a remarkably useful compound as a base material for a medicine from the viewpoint of storage and drug preparation.

BEST MODES FOR CARRYING OUT THE INVENTION

The (S)-(−)-1-(4-fluoroisoquinolin-5-yl)sulfonyl-2-methyl-1,4-homopiperazine hydrochloride dihydrate (2) of the present invention, which is a novel compound, can be produced through the following method.

Firstly, (S)-(−)-1-(4-fluoroisoquinolin-5-yl)sulfonyl-2-methyl-1,4-homopiperazine hydrochloride (1) can be produced through a method as disclosed in Patent Document 1, a reaction scheme of which is shown below.

$L^1$ represents a leaving group

Specifically, (S)-(+)-2-aminopropanol is reacted with a sulfonic acid derivative represented by compound (3) in methylene chloride in the presence of triethylamine, to thereby synthesize compound (4) (first step). Then, the compound (4) is reacted with methanesulfonyl chloride in methylene chloride in the presence of triethylamine, to thereby convert the hydroxyl group to a mesyl group, followed by reacting with 3-aminopropanol, to thereby synthesize compound (5) (second step). The compound (5) is subjected to ring-closure in tetrahydrofuran through the Mitsunobu Reaction employing triphenylphosphine and diisopropyl azodicarboxylate, to thereby synthesize compound (6) (third step). The thus-obtained compound (6) is converted to the corresponding hydrochloride in ethanol by use of a 1N-hydrogen chloride ether solution, to thereby produce (S)-(−)-1-(4-fluoroisoquinolin-5-yl)sulfonyl-2-methyl-1,4-homopiperazine hydrochloride (1).

The (S)-(−)-1-(4-fluoroisoquinolin-5-yl)sulfonyl-2-methyl-1,4-homopiperazine hydrochloride (1) produced through the above procedure is dissolved in water at 50 to 100° C., preferably at 80° C. While the solution is maintained at the temperature, a hydrophilic organic solvent is added to the solution. The resultant mixture is cooled to 0 to 30° C., whereby crystals are precipitated. The crystals are dried at 0 to 30° C. for 20 to 30 hours, to thereby yield (S)-(−)-1-(4-fluoroisoquinolin-5-yl)sulfonyl-2-methyl-1,4-homopiperazine hydrochloride dihydrate (2) of the present invention in the form of crystals.

Preferably, water is used in an amount 1.0 to 2.0 times by weight, more preferably 1.3 to 1.7 times the amount of (S)-(−)-1-(4-fluoroisoquinolin-5-yl)sulfonyl-2-methyl-1,4-homopiperazine hydrochloride (1). The amount of the hydrophilic organic solvent is 2 to 6 times the amount of water added, preferably 4 times.

Examples of the hydrophilic organic solvent include alcohols such as methanol, ethanol, n-propanol, isopropanol, and n-butanol; acetone; N,N-dimethylformamide; dimethylsulfoxide; and diethylene glycol dimethyl ether. Of these, ethanol, isopropanol, and acetone are particularly preferred. The cooling temperature and drying temperature are 0 to 30° C., preferably about room temperature. The drying time is 20 to 30 hours, preferably about 24 hours.

Figure 7:
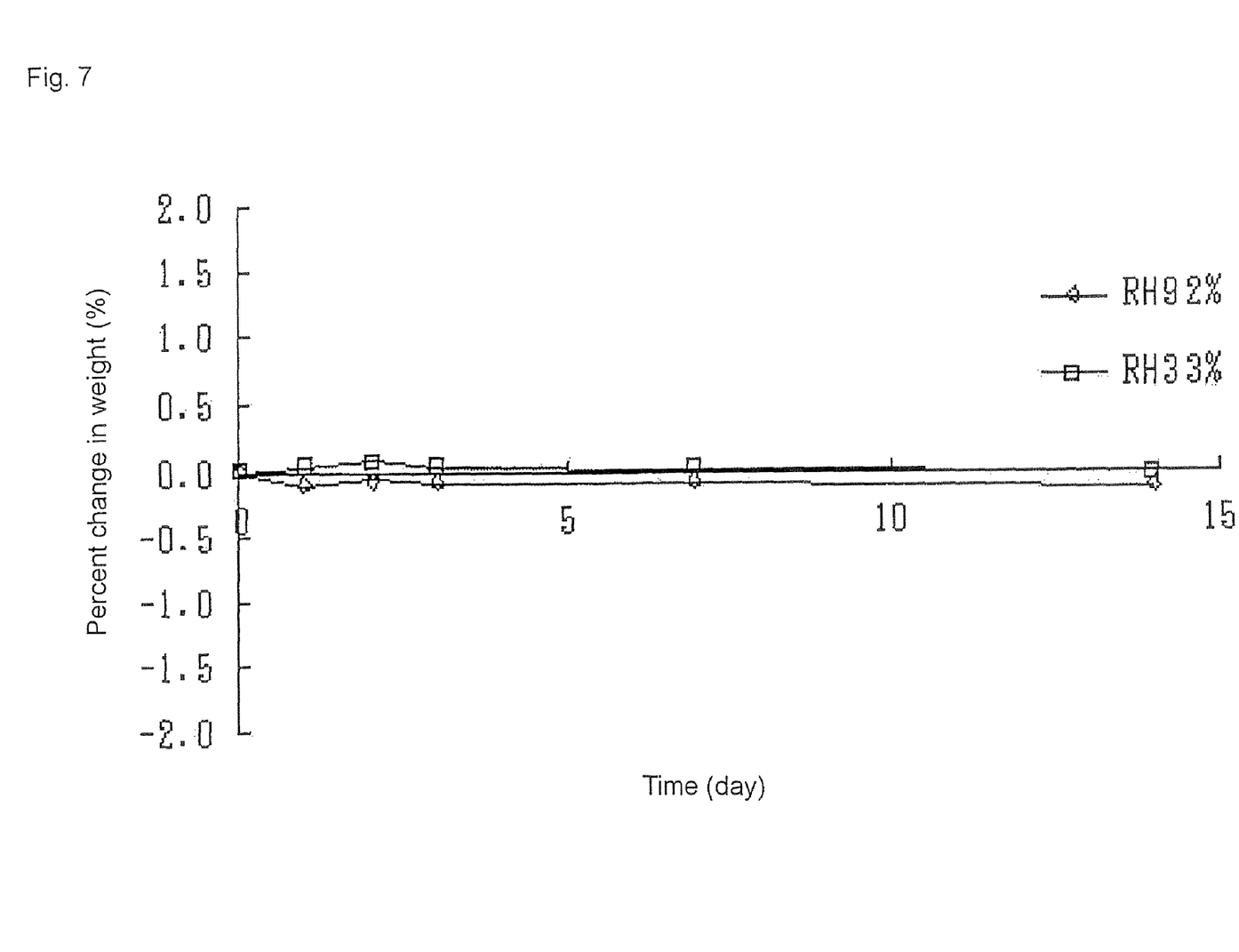
FIG. 7 is a graph showing a hygroscopic behavior (time-dependent change) of (S)-(−)-1-(4-fluoroisoquinolin-5-yl)sulfonyl-2-methyl-1,4-homopiperazine hydrochloride dihydrate.
Figure 8:
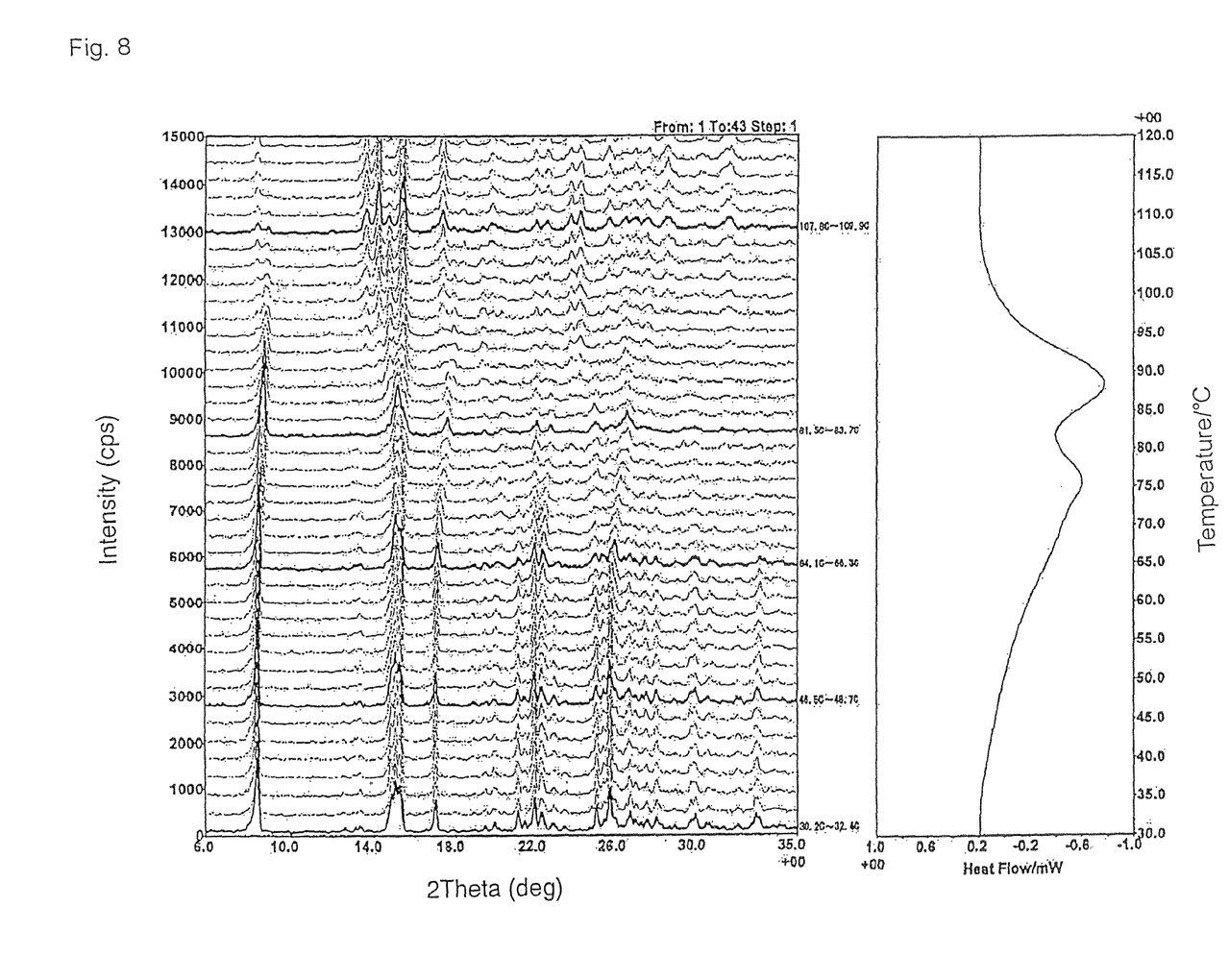
FIG. 8 shows time-dependent change in X-ray powder diffraction pattern of (S)-(−)-1-(4-fluoroisoquinolin-5-yl)sulfonyl-2-methyl-1,4-homopiperazine hydrochloride dihydrate upon temperature elevation for changing water content, and a thermal analysis curve of the hydrate.

The thus-produced dihydrate of the present invention has a water content of 8.80 to 9.40% as determined through Karl Fischer's method, preferably 8.87 to 9.13% as determined through Karl Fischer's method (Tables 4 and 5). As shown in FIG. 7, water content of the dihydrate of the present invention has been found to be constant at 25° C. and a relative humidity of 92% RH for 14 days. Furthermore, the dihydrate of the present invention does not decompose or undergoes undesired reaction even when the dihydrate is stored under severe conditions (i.e., at 80° C. for two weeks) Thus the dihydrate has been found to have high thermal stability (Table 6).

Figure 6:
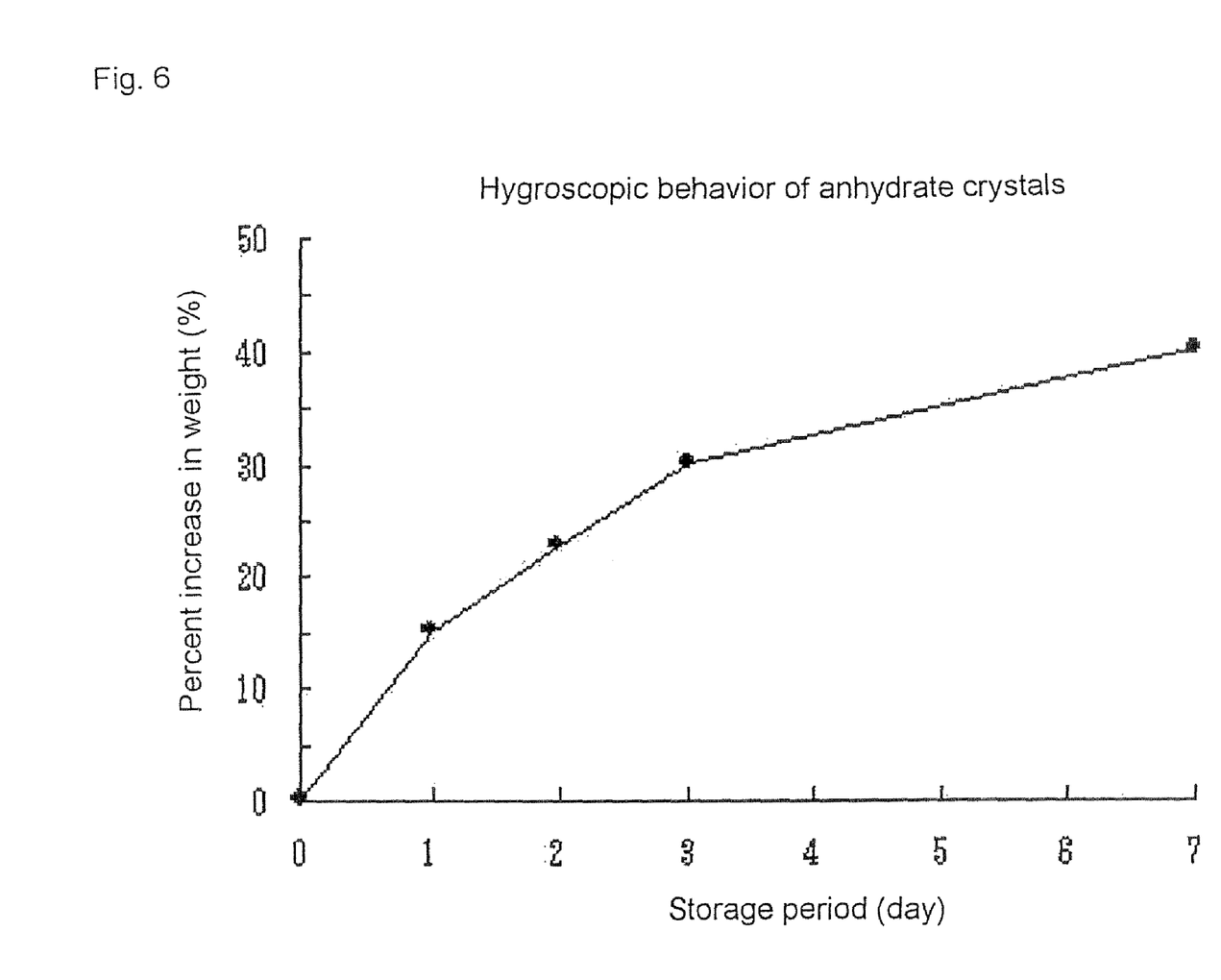
FIG. 6 is a graph showing a hygroscopic behavior (time-dependent change) of (S)-(−)-1-(4-fluoroisoquinolin-5-yl)sulfonyl-2-methyl-1,4-homopiperazine hydrochloride (anhydrous crystals) at 25° C. and a relative humidity of 92%

In contrast, water content of (S)-(−)-1-(4-fluoroisoquinolin-5-yl)sulfonyl-2-methyl-1,4-homopiperazine hydrochloride anhydrate increases with elapsed time under the same conditions. Seven days after, the water content has been increased to 40% (FIG. 6).

The dihydrate of the present invention is a useful active ingredient contained in a drug for preventing or treating diseases originating from a cerebrovascular disorder such as cerebral infarction, cerebral hemorrhage, subarachnoid hemorrhage, and cerebral edema. No particular limitation is imposed on the type of administration of the dihydrate of the present invention, and either oral administration or parenteral administration (e.g., intramuscular, subcutaneous, intravenous, suppository, eye drops) may be employed.

In the case where a peroral formulation is prepared, excipient and, in accordance with needs, a pharmaceutically acceptable carrier such as a binder, a disintegrant, a lubricant, a coloring agent, or a sweetening/flavoring agent is added to the dihydrate. The mixture may be formed into tablets, coated tablet, granules, capsules, solution, syrup, elixir, or oil- or water-soluble suspension through a routine method.

Examples of the excipient include lactose, corn starch, white sugar, glucose, sorbitol, and crystalline cellulose. Examples of the binder include polyvinyl alcohol, polyvinyl ether, ethyl cellulose, methyl cellulose, gum arabic, tragacanth gum, gelatin, shellac, hydroxypropyl cellulose, hydroxypropyl starch, and polyvinyl pyrrolidone.

Examples of the disintegrant include starch, agar, gelatin powder, crystalline cellulose, calcium carbonate, sodium hydrogencarbonate, calcium citrate, dextran, and pectin. Examples of the lubricant include sodium stearate, talc, polyethylene glycol, silica, and hardened vegetable oil. As a coloring agent, those which are acceptable to use in drugs may be employed. Examples of the sweetening/flavoring agent which may be used include cocoa powder, menthol, aromatic acid, peppermint oil, borneol, and cinnamon powder. In accordance with needs, these tablets and granules may be appropriately coated with sugar, gelatin, or other materials.

When injections and eye drops are prepared, an additive such as a pH regulator, a buffer, a stabilizer, or a preservative is added to the dihydrate in accordance with needs. Through a routine method, the mixture is formed into subcutaneous injections, intramuscular injections, or intravenous injections. In an alternative embodiment, a drug solution such as an injection or eye drops preparation is charged into a container, and through lyophilization or a similar technique, is formed into a solid preparation, which is reconstituted upon use. One dose may be placed in a single container. Alternatively, a plurality of doses may be placed in a single container.

The dihydrate of the present invention is generally administered to an adult human at a daily dose of 0.01 to 1000 mg, preferably 0.1 to 100 mg. The daily dose may be administered once a day or 2 to 4 divided times a day.

EXAMPLES

The present invention will next be described in more detail by way of examples and test examples, which should not be construed as limiting the invention thereto.

Example 1

(S)-(−)-1-(4-fluoroisoquinolin-5-yl)sulfonyl-2-methyl-1,4-homopiperazine hydrochloride (1) (2.0 g) prepared through the method described in the pamphlet of International Publication WO 99/20620 was dissolved in water (3 mL) under heating at 80° C. Subsequently, isopropanol (12 mL) was added to the solution under heating. After the mixture had been confirmed to be homogeneous, the mixture was allowed to stand overnight at room temperature for crystallization. The thus-precipitated crystals were collected through filtration, followed by drying at room temperature for 24 hours, to thereby yield 1.76 g of (S)-(−)-1-(4-fluoroisoquinolin-5-yl)sulfonyl-2-methyl-1,4-homopiperazine hydrochloride dihydrate (80.0%).

Elemental analysis: as $C_{15}H_{18}N_3O_2FS \cdot HCl \cdot 2H_2O$

Calculated: C 45.51%; H 5.86%; N 10.61%; Cl 8.96%

Found: C 45.50%; H 5.84%; N 10.57%; Cl 8.93%

Figure 1:
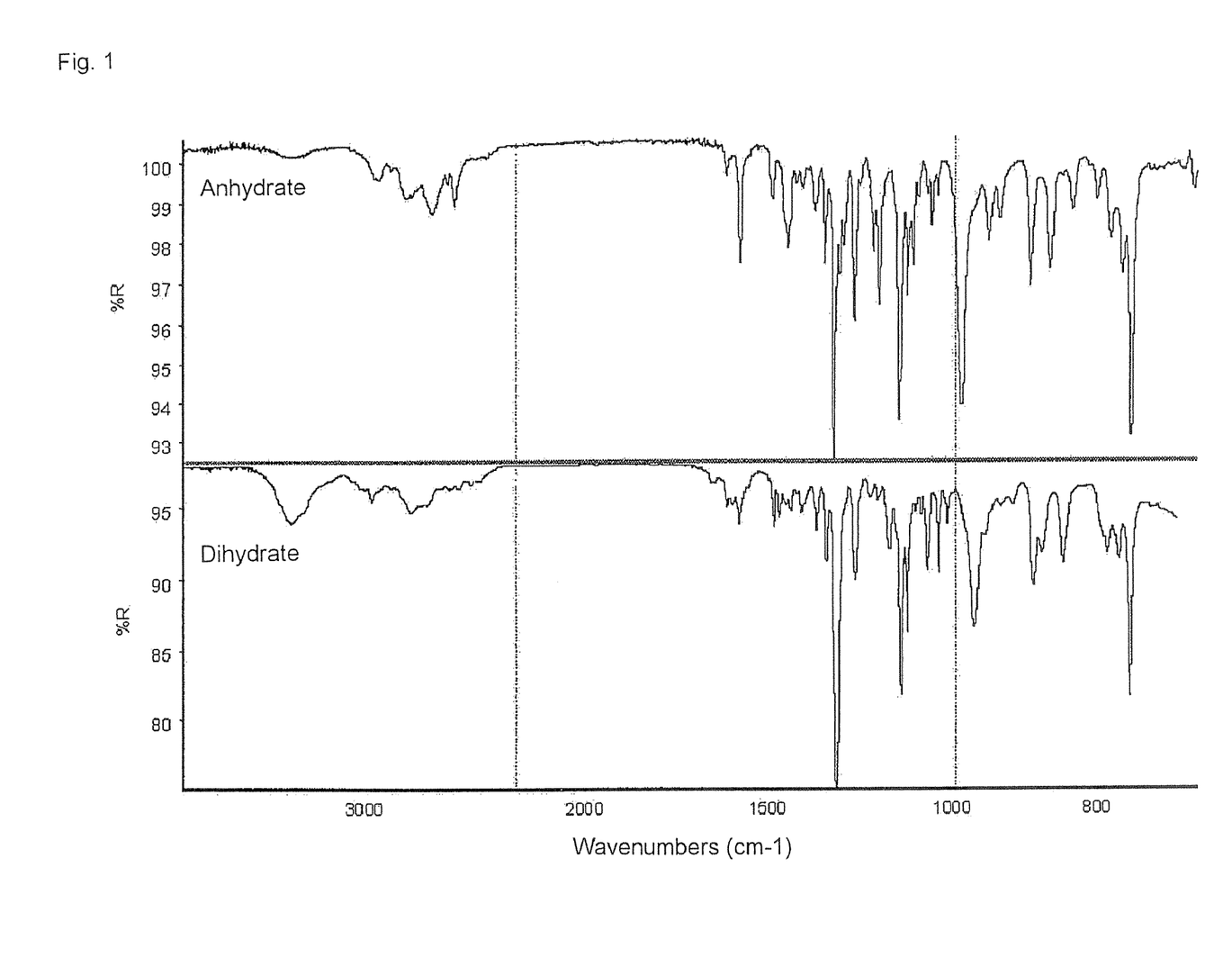
FIG. 1 is a chart showing an infrared absorption spectrum of (S)-(−)-1-(4-fluoroisoquinolin-5-yl)sulfonyl-2-methyl-1,4-homopiperazine hydrochloride (anhydrous crystals) (top) and that of (S)-(−)-1-(4-fluoroisoquinolin-5-yl)sulfonyl-2-methyl-1,4-homopiperazine hydrochloride dihydrate (bottom).

The infrared absorption spectrum of the dihydrate measured by means of an infrared spectrophotometer (AVATAR370, product of Thermo Nicolet; ATR method) exhibits absorption peaks attributable to dihydrate virtually at 854, 974, 1146, 1323, and 3418 $cm^{-1}$ (FIG. 1, bottom). Specific data of wave number and intensity of the peaks are shown in Table 1. The absorption spectrum of the corresponding anhydrous crystals is shown in FIG. 1 (top) and the absorption peaks are shown in Table 2.

TABLE 1

Infrared absorption of dihydrate
(Wave number: cm$^{-1}$, Intensity: % R)

| Wave number: | 764.51 | Intensity: | 80.630 |
|---|---|---|---|
| Wave number: | 779.76 | Intensity: | 91.146 |
| Wave number: | 794.63 | Intensity: | 91.621 |
| Wave number: | 854.41 | Intensity: | 90.857 |
| Wave number: | 882.98 | Intensity: | 91.724 |
| Wave number: | 894.42 | Intensity: | 89.039 |
| Wave number: | 974.74 | Intensity: | 86.245 |
| Wave number: | 1020.91 | Intensity: | 93.720 |
| Wave number: | 1043.96 | Intensity: | 90.273 |
| Wave number: | 1074.70 | Intensity: | 90.454 |
| Wave number: | 1092.36 | Intensity: | 94.291 |
| Wave number: | 1130.49 | Intensity: | 86.130 |
| Wave number: | 1146.17 | Intensity: | 81.445 |
| Wave number: | 1178.81 | Intensity: | 91.941 |
| Wave number: | 1272.85 | Intensity: | 89.759 |
| Wave number: | 1323.30 | Intensity: | 75.088 |
| Wave number: | 1350.82 | Intensity: | 91.048 |
| Wave number: | 1377.13 | Intensity: | 93.358 |
| Wave number: | 1418.51 | Intensity: | 94.514 |
| Wave number: | 1448.58 | Intensity: | 94.730 |
| Wave number: | 1479.05 | Intensity: | 94.217 |
| Wave number: | 1494.35 | Intensity: | 93.546 |
| Wave number: | 1588.71 | Intensity: | 93.721 |
| Wave number: | 2774.45 | Intensity: | 94.646 |
| Wave number: | 2984.37 | Intensity: | 95.357 |
| Wave number: | 3418.71 | Intensity: | 93.908 |

TABLE 2

Infrared absorption of anhydrate
(Wave number: cm$^{-1}$, Intensity: % R)

| Wave number: | 679.34 | Intensity: | 99.252 |
|---|---|---|---|
| Wave number: | 762.59 | Intensity: | 92.637 |
| Wave number: | 773.67 | Intensity: | 97.136 |
| Wave number: | 790.25 | Intensity: | 97.978 |
| Wave number: | 807.65 | Intensity: | 99.013 |
| Wave number: | 840.68 | Intensity: | 98.725 |
| Wave number: | 871.31 | Intensity: | 97.249 |
| Wave number: | 898.03 | Intensity: | 96.797 |
| Wave number: | 939.89 | Intensity: | 98.506 |
| Wave number: | 954.86 | Intensity: | 97.913 |
| Wave number: | 992.25 | Intensity: | 93.757 |
| Wave number: | 1044.93 | Intensity: | 99.087 |
| Wave number: | 1061.07 | Intensity: | 98.394 |
| Wave number: | 1073.37 | Intensity: | 99.155 |
| Wave number: | 1098.17 | Intensity: | 99.056 |
| Wave number: | 1112.48 | Intensity: | 97.383 |
| Wave number: | 1129.22 | Intensity: | 96.590 |
| Wave number: | 1151.65 | Intensity: | 93.492 |
| Wave number: | 1205.14 | Intensity: | 96.423 |
| Wave number: | 1221.03 | Intensity: | 97.745 |
| Wave number: | 1273.55 | Intensity: | 95.943 |
| Wave number: | 1301.49 | Intensity: | 97.917 |
| Wave number: | 1314.42 | Intensity: | 97.117 |
| Wave number: | 1329.07 | Intensity: | 92.494 |
| Wave number: | 1354.18 | Intensity: | 97.487 |
| Wave number: | 1381.27 | Intensity: | 98.752 |
| Wave number: | 1414.12 | Intensity: | 99.324 |
| Wave number: | 1455.71 | Intensity: | 97.838 |
| Wave number: | 1497.05 | Intensity: | 99.039 |
| Wave number: | 1586.02 | Intensity: | 97.437 |
| Wave number: | 1623.73 | Intensity: | 99.643 |
| Wave number: | 2534.92 | Intensity: | 98.913 |
| Wave number: | 2648.09 | Intensity: | 98.692 |
| Wave number: | 2797.78 | Intensity: | 99.062 |
| Wave number: | 2945.10 | Intensity: | 99.554 |

Figure 2:
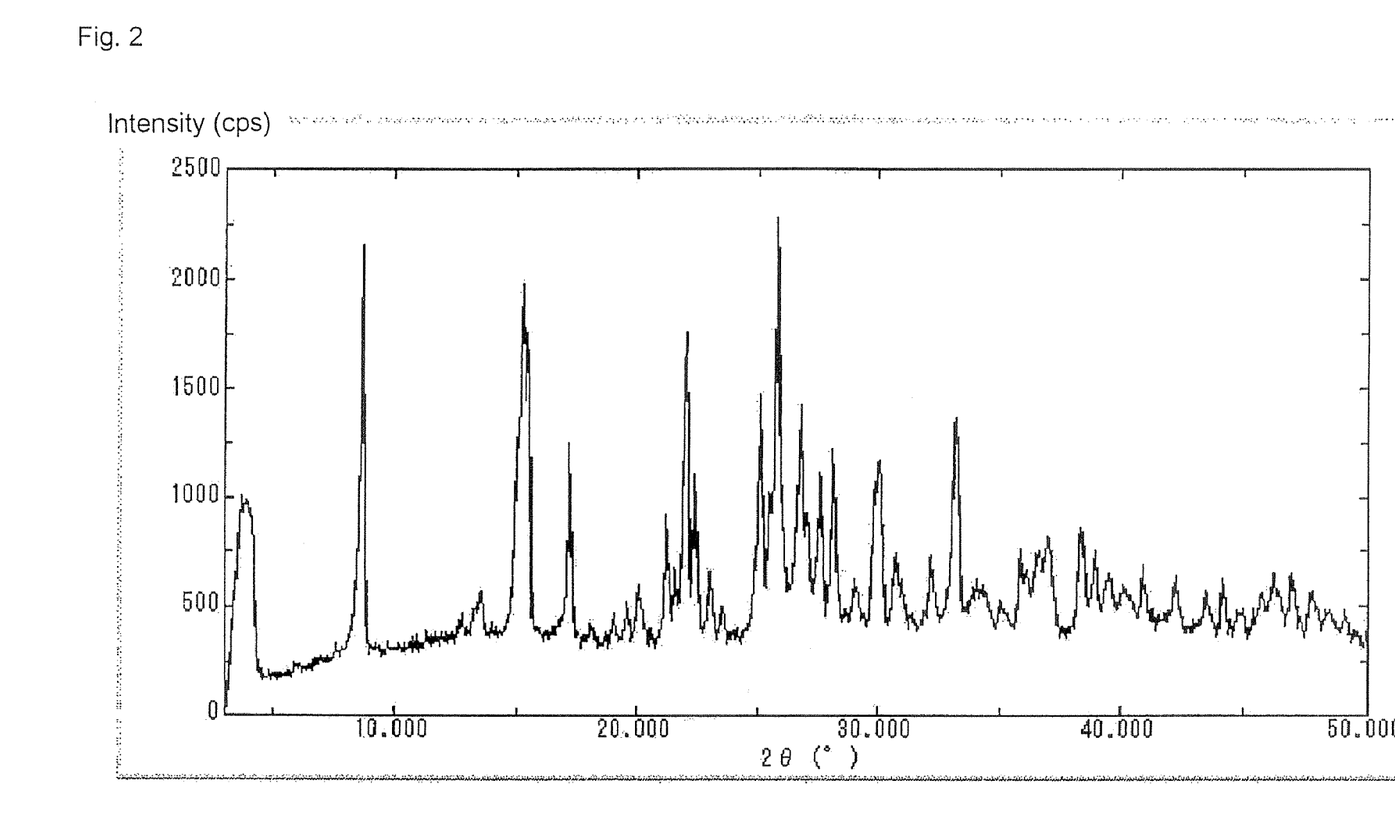
FIG. 2 is a chart showing a X-ray powder diffraction pattern of (S)-(−)-1-(4-fluoroisoquinolin-5-yl)sulfonyl-2-methyl-1,4-homopiperazine hydrochloride dihydrate.

FIG. 2 shows a X-ray powder diffraction pattern of the dihydrate obtained by means of a diffractometer (Miniflex, product of Rigaku Denki Kogyo) The apparatus was used in the following procedure. As shown in Table 3, X-ray diffraction peaks attributable to dihydrate were observed at diffraction angles (2θ) of 8.660, 15.240, 17.180, 25.100, 25.780, 26.780, 28.100, 30.060, and 33.200°. Width at half-height (at ½ intensity), crystaline plane spacing (d value), diffraction X-ray intensity (intensity), and diffraction X-ray relative intensity (relative intensity) of the peaks are also shown in Table 3.

Figure 3:
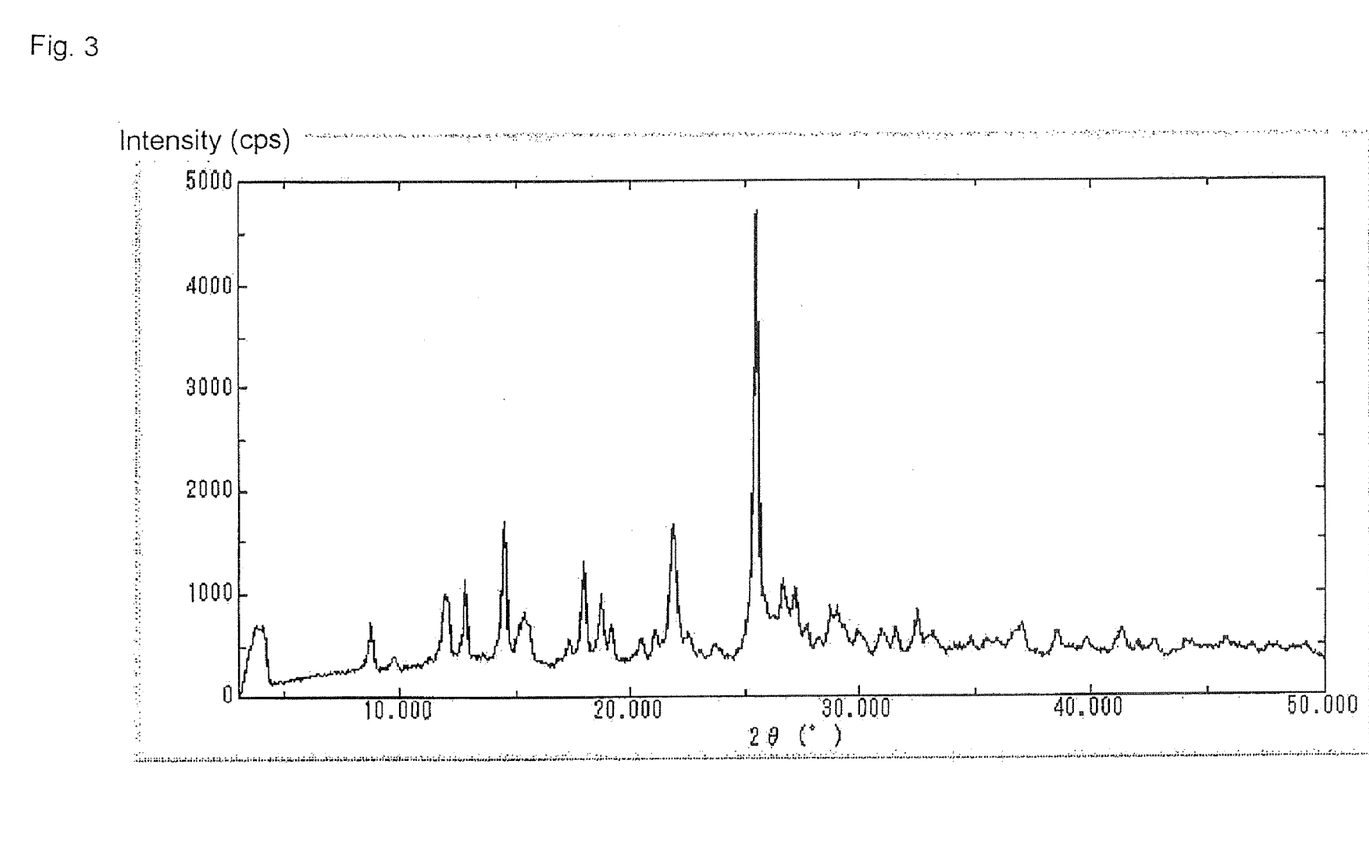
FIG. 3 is a chart showing a X-ray powder diffraction pattern of (S)-(−)-1-(4-fluoroisoquinolin-5-yl)sulfonyl-2-methyl-1,4-homopiperazine hydrochloride (anhydrous crystals).

The X-ray powder diffraction pattern of the corresponding anhydrate is shown in FIG. 3, and diffraction angle, Width at half-height, d value, intensity, and relative intensity of the diffraction peaks are shown in Table 4.

TABLE 3

Diffraction angles of dihydrate

| Peak number | 2θ | Width at half-height | d | Intensity | Relative intensity |
|---|---|---|---|---|---|
| 1 | 3.420 | 0.141 | 25.8122 | 571 | 26 |
| 2 | 3.700 | 0.118 | 23.8595 | 1002 | 45 |
| 3 | 3.900 | 0.165 | 22.6364 | 991 | 44 |
| 4 | 4.140 | 0.212 | 21.3246 | 878 | 39 |
| 5 | 8.060 | 0.118 | 10.9600 | 360 | 16 |
| 6 | 8.660 | 0.165 | 10.2019 | 2151 | 96 |
| 7 | 12.780 | 0.118 | 6.9208 | 469 | 21 |
| 8 | 13.240 | 0.165 | 6.6814 | 487 | 22 |
| 9 | 13.540 | 0.165 | 6.5340 | 543 | 25 |
| 10 | 15.020 | 0.188 | 5.8933 | 1269 | 57 |
| 11 | 15.240 | 0.165 | 5.8088 | 1955 | 87 |
| 12 | 15.460 | 0.141 | 5.7266 | 1759 | 78 |
| 13 | 17.180 | 0.188 | 5.1569 | 1184 | 53 |
| 14 | 19.560 | 0.212 | 4.5345 | 520 | 24 |
| 15 | 20.040 | 0.235 | 4.4270 | 596 | 27 |
| 16 | 21.180 | 0.188 | 4.1912 | 916 | 41 |
| 17 | 21.540 | 0.165 | 4.1219 | 674 | 30 |
| 18 | 21.980 | 0.188 | 4.0404 | 1757 | 78 |
| 19 | 22.380 | 0.188 | 3.9691 | 1100 | 49 |
| 20 | 23.000 | 0.212 | 3.8635 | 653 | 29 |
| 21 | 24.860 | 0.118 | 3.5785 | 714 | 32 |
| 22 | 25.100 | 0.212 | 3.5448 | 1471 | 66 |
| 23 | 25.460 | 0.165 | 3.4955 | 1031 | 46 |
| 24 | 25.780 | 0.165 | 3.4528 | 2258 | 100 |
| 25 | 26.780 | 0.165 | 3.3261 | 1425 | 64 |
| 26 | 27.060 | 0.188 | 3.2923 | 875 | 39 |
| 27 | 27.600 | 0.165 | 3.2291 | 1112 | 50 |
| 28 | 28.100 | 0.212 | 3.1728 | 1219 | 54 |
| 29 | 29.000 | 0.141 | 3.0763 | 610 | 27 |
| 30 | 29.100 | 0.118 | 3.0660 | 570 | 26 |
| 31 | 29.840 | 0.141 | 2.9916 | 1079 | 48 |
| 32 | 30.060 | 0.188 | 2.9702 | 1157 | 52 |
| 33 | 30.700 | 0.188 | 2.9098 | 745 | 33 |
| 34 | 30.980 | 0.141 | 2.8841 | 628 | 28 |
| 35 | 32.160 | 0.165 | 2.7809 | 732 | 15 |
| 36 | 32.800 | 0.118 | 2.7281 | 575 | 26 |
| 37 | 33.200 | 0.282 | 2.6961 | 1339 | 60 |
| 38 | 34.260 | 0.118 | 2.6151 | 577 | 26 |
| 39 | 35.840 | 0.188 | 2.5034 | 738 | 33 |
| 40 | 36.100 | 0.165 | 2.4859 | 669 | 30 |
| 41 | 36.620 | 0.118 | 2.4518 | 739 | 33 |
| 42 | 37.700 | 0.235 | 2.4275 | 806 | 36 |
| 43 | 38.320 | 0.212 | 2.3469 | 823 | 37 |
| 44 | 38.900 | 0.165 | 2.3122 | 750 | 34 |
| 45 | 39.340 | 0.118 | 2.2883 | 605 | 27 |
| 46 | 39.480 | 0.212 | 2.2805 | 628 | 28 |
| 47 | 39.580 | 0.118 | 2.2750 | 595 | 27 |
| 48 | 40.900 | 0.306 | 2.2046 | 674 | 30 |
| 49 | 42.260 | 0.118 | 2.1367 | 637 | 29 |
| 50 | 44.160 | 0.235 | 2.0491 | 610 | 27 |
| 51 | 46.240 | 0.212 | 1.9646 | 614 | 28 |
| 52 | 46.460 | 0.118 | 1.9529 | 563 | 25 |
| 53 | 46.940 | 0.235 | 1.9340 | 627 | 28 |

TABLE 4

Diffraction angles of anhydrate

| Peak number | 2θ | Width at half-height | d | Intensity | Relative intensity |
|---|---|---|---|---|---|
| 1 | 3.520 | 0.165 | 25.0791 | 488 | 11 |
| 2 | 3.800 | 0.118 | 23.2318 | 719 | 16 |
| 3 | 4.120 | 0.259 | 21.4281 | 698 | 15 |
| 4 | 8.700 | 0.212 | 10.1551 | 729 | 16 |
| 5 | 9.720 | 0.235 | 9.0916 | 389 | 9 |
| 6 | 11.240 | 0.118 | 7.8653 | 386 | 9 |
| 7 | 11.560 | 0.118 | 7.6483 | 452 | 10 |
| 8 | 11.880 | 0.212 | 7.4430 | 973 | 21 |
| 9 | 12.040 | 0.141 | 7.3445 | 972 | 21 |
| 10 | 12.780 | 0.212 | 6.9208 | 1140 | 25 |
| 11 | 13.140 | 0.141 | 6.7320 | 414 | 9 |
| 12 | 13.340 | 0.118 | 6.6315 | 424 | 9 |
| 13 | 14.480 | 0.188 | 6.1119 | 1696 | 36 |
| 14 | 15.320 | 0.165 | 5.7786 | 812 | 18 |
| 15 | 15.560 | 0.165 | 5.6900 | 712 | 16 |
| 16 | 17.260 | 0.188 | 5.1332 | 569 | 13 |
| 17 | 17.920 | 0.212 | 4.9456 | 1310 | 28 |
| 18 | 18.680 | 0.212 | 4.7461 | 1003 | 22 |
| 19 | 19.120 | 0.212 | 4.6378 | 712 | 16 |
| 20 | 20.400 | 0.188 | 4.3496 | 582 | 13 |
| 21 | 21.020 | 0.259 | 4.2227 | 650 | 14 |
| 22 | 21.340 | 0.118 | 4.1601 | 561 | 12 |
| 23 | 21.840 | 0.259 | 4.0660 | 1668 | 36 |
| 24 | 21.860 | 0.118 | 4.0623 | 1643 | 35 |
| 25 | 22.500 | 0.212 | 3.9482 | 607 | 13 |
| 26 | 25.480 | 0.212 | 3.4928 | 4713 | 100 |
| 27 | 25.840 | 0.165 | 3.4449 | 957 | 21 |
| 28 | 26.220 | 0.141 | 3.3959 | 768 | 17 |
| 29 | 26.620 | 0.188 | 3.3457 | 1125 | 24 |
| 30 | 27.160 | 0.235 | 3.2804 | 1044 | 23 |
| 31 | 27.700 | 0.118 | 3.2177 | 704 | 15 |
| 32 | 28.180 | 0.165 | 3.1640 | 569 | 13 |
| 33 | 28.700 | 0.141 | 3.1078 | 892 | 19 |
| 34 | 29.000 | 0.118 | 3.0763 | 879 | 19 |
| 35 | 29.320 | 0.165 | 3.0435 | 695 | 15 |
| 36 | 29.880 | 0.188 | 2.9877 | 643 | 14 |
| 37 | 30.940 | 0.188 | 2.8877 | 654 | 14 |
| 38 | 31.560 | 0.259 | 2.8324 | 677 | 15 |
| 39 | 32.480 | 0.235 | 2.7542 | 837 | 18 |
| 40 | 32.980 | 0.118 | 2.7136 | 595 | 13 |
| 41 | 34.800 | 0.141 | 2.5758 | 590 | 13 |
| 42 | 36.560 | 0.118 | 2.4557 | 620 | 14 |
| 43 | 36.980 | 0.165 | 2.4288 | 710 | 16 |
| 44 | 38.520 | 0.259 | 2.3351 | 623 | 14 |
| 45 | 41.300 | 0.353 | 2.1841 | 653 | 14 |
| 46 | 45.820 | 0.235 | 1.9786 | 559 | 12 |

Figure 4:
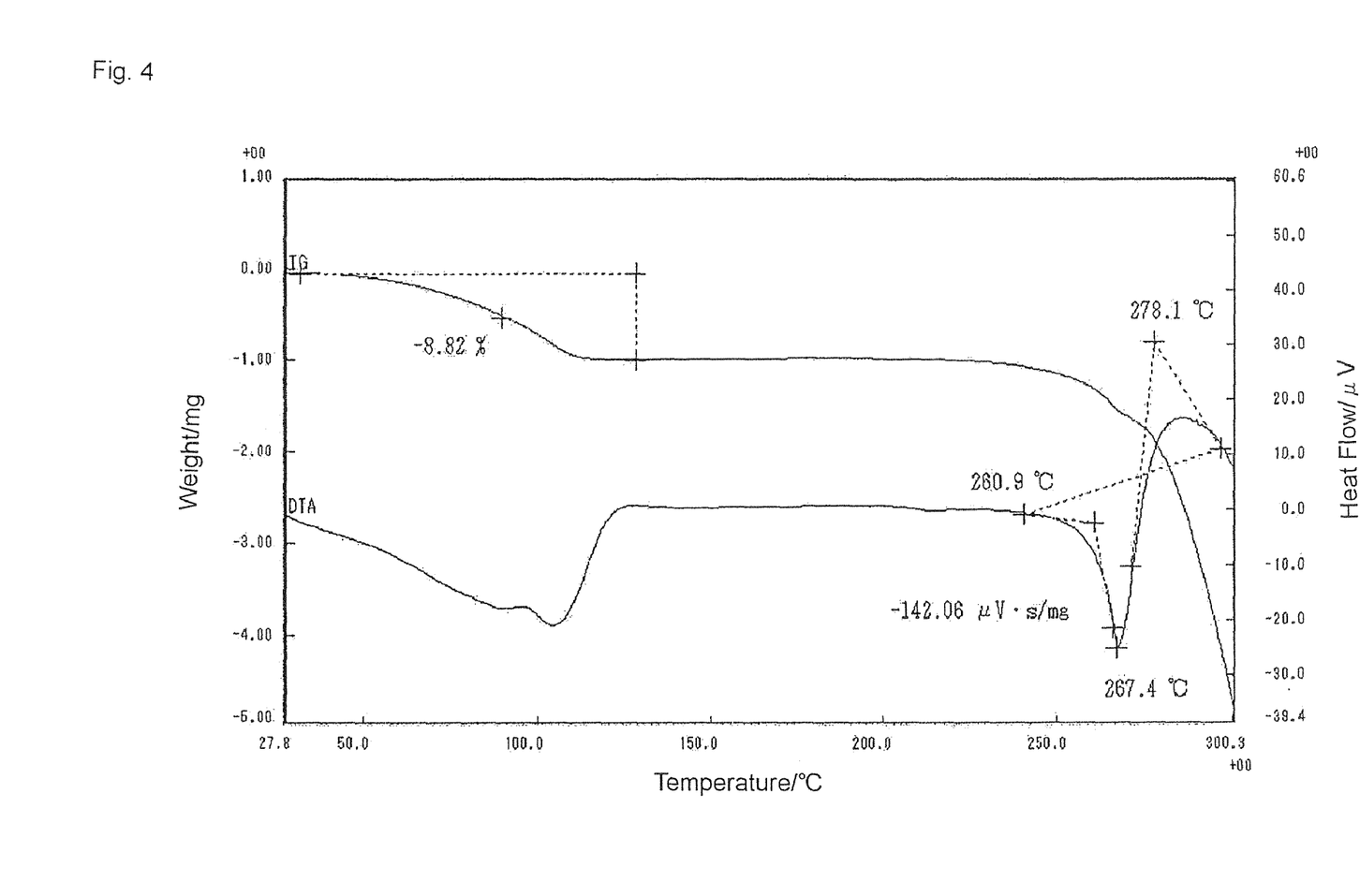
FIG. 4 is a graph showing thermal analyses of (S)-(−)-1-(4-fluoroisoquinolin-5-yl)sulfonyl-2-methyl-1,4-homopiperazine hydrochloride dihydrate.

FIGS. 4 and 5 show the results of thermal analysis out by means of an analyzer (XRD-DSC, product of Denki Kogyo).

Example 2

The procedure of Example 1 was repeated, except that ethanol was used instead of isopropanol, to thereby yield (S)-(−)-1-(4-fluoroisoquinolin-5-yl)sulfonyl-2-methyl-1,4-homopiperazine hydrochloride dihydrate (2).

Example 3

(S)-(−)-1-(4-fluoroisoquinolin-5-yl)sulfonyl-2-methyl-1,4-homopiperazine hydrochloride (1) (50.0 g) was dissolved in water (75 mL) under heating at 80° C. Subsequently, acetone (300 mL) was added to the solution under heating. After the mixture had been confirmed to be homogeneous, the mixture was allowed to stand overnight at room temperature for crystallization. The thus-precipitated crystals were collected through filtration, followed by drying at room temperature for 24 hours, to thereby yield 45.4 g of (S)-(−)-1-(4-fluoroisoquinolin-5-yl)sulfonyl-2-methyl-1,4-homopiperazine hydrochloride dihydrate (2) (82.5%).

mp 258° C.

Elemental analysis: as $C_{15}H_{18}N_3O_2FS \cdot HCl \cdot 2H_2O$

Calculated: C 45.51%; H 5.86%; N 10.61%; Cl 8.96%

Found: C 45.49%; H 5.82%; N 10.56%; Cl 8.95%

Test Example 1 (Thermal Stability)

The dihydrate of the present invention produced in Example 1 was placed in sealable containers such that each container included 1 g of the dihydrate. After sealing, these containers were maintained in thermostats at 40, 60, and 80° C. for 7 and 14 days, so as to evaluate thermal stability. Table 5 shows the results.

TABLE 5

| Storage temp. | Storage period | Percent remain (%) |
|---|---|---|
| 40° C. | 7 days | 100.0 |
|  | 14 days | 99.6 |
| 60° C. | 7 days | 99.6 |
|  | 14 days | 99.8 |
| 80° C. | 7 days | 99.8 |
|  | 14 days | 99.8 |

As is clear from Table 5, the dihydrate of the present invention exhibits high thermal stability even after storage at 40° C., 60° C., or 80° C. for two weeks.

Test Example 2 (Hygroscopicity)

Each of the dihydrate of the present invention produced in Example 1 and (S)-(−)-1-(4-fluoroisoquinolin-5-yl)sulfonyl-2-methyl-1,4-homopiperazine hydrochloride anhydrate (each 100 mg) was placed in a weighing bottle. The bottle was allowed to stand in a container maintained at 25° C. and an RH of 33% or 92%, with the container being opened. The weighing bottle was time-dependently weighed, to thereby determine increase in weight for evaluation of hygroscopicity. FIGS. 6 and 7 show the results.

As is clear from FIGS. 6 and 7, water content of the anhydrate increased from 0 to 40% with elapse of time, indicating poor hygroscopic stability. In contrast, the dihydrate of the present invention exhibited no change in its water content, indicating excellent hygroscopic stability. The dihydrate of the present invention was still stable even after storage for two weeks under the same conditions.

The results of elemental analysis, water content, X-ray powder diffraction, and infrared absorption spectrum of the dihydrate of the present invention produced in Examples 1 to 3 are collectively shown in Table 6.

TABLE 6

|  | Organic solvent | | |
|---|---|---|---|
|  | Isopropanol | Ethanol | Acetone |
| Elemental analysis (C, H, N, Cl) | Ex. 1* | Ex. 1** | Ex. 3* |
| Water content (%) | 9.05 | 9.13 | 8.94 |

TABLE 6-continued

| | Organic solvent | | |
|---|---|---|---|
| | Isopropanol | Ethanol | Acetone |
| X-ray powder diffraction | Ex. 1* | Ex. 1** | Ex. 1** |
| IR absorption spectrum | Ex. 1* | Ex. 1** | Ex. 1** |

*described in
**coinciding with

As is clear from Table 6, when ethanol or acetone was employed as an organic solvent instead of isopropanol, the same elemental analysis results, water content, X-ray powder diffraction results, and infrared absorption spectrum as those of the dihydrate were obtained.

Example 4 (Reproducibility on a Large Scale)

In a manner similar to that of Example 3, two more lots of the dihydrate of the present invention were produced. Reproducibility in physical properties was confirmed. Table 7 shows the results.

TABLE 7

| | Lot | | |
|---|---|---|---|
| | 1 (Ex. 3) | 2 | 3 |
| Elemental analysis (C, H, N, Cl) | Ex. 3* | Ex. 3** | Ex. 3** |
| Water content (%) | 8.87 | 8.89 | 8.90 |
| X-ray powder diffraction | Ex. 1** | Ex. 1** | Ex. 1** |
| IR absorption spectrum | Ex. 1** | Ex. 1** | Ex. 1** |

*described in
**coinciding with
Note:
Lot No. 1 refers to the dihydrate obtained in Example 3

As is clear from Table 7, all the lots exhibited the physical properties including elemental analysis, water content, X-ray powder diffraction, and infrared absorption spectrum, characteristic to the dihydrate. The results indicate that the dihydrate of the present invention can be produced with high reproducibility in large-scale production.

The invention claimed is:

1. (S)-(−)-1-(4-fluoroisoquinolin-5-yl)sulfonyl-2-methyl-1,4-homopiperazine hydrochloride dihydrate.

2. (S)-(−)-1-(4-fluoroisoquinolin-5-yl)sulfonyl-2-methyl-1,4-homopiperazine hydrochloride dihydrate as described in claim 1, which has a water content of 8.80 to 9.40%, as determined through Karl Fischer's method.

3. (S)-(−)-1-(4-fluoroisoquinolin-5-yl)sulfonyl-2-methyl-1,4-homopiperazine hydrochloride dihydrate as described in claim 1, which exhibits characteristic peaks, in a X-ray powder diffraction pattern, at diffraction angle (2θ) of 8.660, 15.240, 17.180, 25.100, 25.780, 26.780, 28.100, 30.060, and 33.200°.

4. (S)-(−)-1-(4-fluoroisoquinolin-5-yl)sulfonyl-2-methyl-1,4-homopiperazine hydrochloride dihydrate as described in claim 1, which exhibits characteristic absorption peaks, in an infrared absorption spectrum, at near 854, 974, 1146, 1323, and 3418 $cm^{-1}$.

5. A method for producing (S)-(−)-1-(4-fluoroisoquinolin-5-yl)sulfonyl-2-methyl-1,4-homopiperazine hydrochloride dihydrate as recited in claim 1, comprising dissolving (S)-(−)-1-(4-fluoroisoquinolin-5-yl)sulfonyl-2-methyl-1,4-homopiperazine hydrochloride in water at 50 to 100° C., subsequently, adding a hydrophilic organic solvent to the solution, and cooling the mixture to 0 to 30° C.

6. The method for producing (S)-(−)-1-(4-fluoroisoquinolin-5-yl)sulfonyl-2-methyl-1,4-homopiperazine hydrochloride dihydrate as described in claim 5, wherein water is used in an amount 1.0 to 2.0 times by weight with respect to (S)-(−)-1-(4-fluoroisoquinolin-5-yl)sulfonyl-2-methyl-1,4-homopiperazine hydrochloride.

7. The method for producing (S)-(−)-1-(4-fluoroisoquinolin-5-yl)sulfonyl-2-methyl-1,4-homopiperazine hydrochloride dihydrate as described in claim 5, wherein the ratio by weight of water to the hydrophilic organic solvent is 1:2 to 1:6.

8. A composition comprising (S)-(−)-1-(4-fluoroisoquinolin-5-yl)sulfonyl-2-methyl-1,4-homopiperazine hydrochloride dihydrate and a pharmaceutically acceptable carrier.

9. A method for treating a cerebrovascular disorder selected from the group consisting of cerebral infarction, cerebral hemorrhage, subarachnoid hemorrhage, and cerebral edema comprising administering to a subject in need thereof an effective amount of (S)-(−)-1-(4-fluoroisoquinolin-5-yl)sulfonyl-2-methyl-1,4-homopiperazine hydrochloride dihydrate.

10. A method of manufacturing a medicine comprising adding (S)-(−) -1-(4-fluoroisoquinolin-5-yl)sulfonyl-2-methyl-1,4-homopiperazine hydrochloride dehydrate to a composition comprising pharmaceutical acceptable excipients.

* * * * *

UNITED STATES PATENT AND TRADEMARK OFFICE
CERTIFICATE OF CORRECTION

PATENT NO. : 7,858,615 B2
APPLICATION NO. : 11/720288
DATED : December 28, 2010
INVENTOR(S) : Takeshi Ohshima et al.

It is certified that error appears in the above-identified patent and that said Letters Patent is hereby corrected as shown below:

Please change the following:

In column 12, line 49, "dehydrate" should read -- dihydrate --.

Signed and Sealed this
Twenty-second Day of March, 2011

David J. Kappos
*Director of the United States Patent and Trademark Office*